United States Patent
Leuthardt et al.

(10) Patent No.: US 10,596,014 B2
(45) Date of Patent: Mar. 24, 2020

(54) METHODS AND SYSTEMS FOR CONTROLLING BODY PARTS AND DEVICES USING IPSILATERAL MOTOR CORTEX AND MOTOR RELATED CORTEX

(71) Applicant: Washington University, St. Louis, MO (US)

(72) Inventors: Eric Claude Leuthardt, St. Louis, MO (US); Kimberly Kreines, St. Louis, MO (US); Nick Anderson, Iowa City, IA (US)

(73) Assignee: Washington University, St. Louis, MO (US)

( * ) Notice: Subject to any disclaimer, the term of this patent is extended or adjusted under 35 U.S.C. 154(b) by 49 days.

(21) Appl. No.: 15/644,201

(22) Filed: Jul. 7, 2017

(65) Prior Publication Data
US 2017/0304084 A1 Oct. 26, 2017

Related U.S. Application Data

(63) Continuation of application No. 14/291,603, filed on May 30, 2014, now Pat. No. 9,730,816, which is a
(Continued)

(51) Int. Cl.
*A61F 2/72* (2006.01)
*A61B 5/00* (2006.01)
(Continued)

(52) U.S. Cl.
CPC ............ *A61F 2/72* (2013.01); *A61B 5/04001* (2013.01); *A61B 5/4076* (2013.01); *A61B 5/4836* (2013.01); *A61F 2/042* (2013.01); *A61F 2/50* (2013.01); *A61F 2002/482* (2013.01); *A61F 2002/6872* (2013.01); *A61F 2002/704* (2013.01); *A61F 2002/7615* (2013.01);
(Continued)

(58) Field of Classification Search
CPC ... A61F 2/72; A61F 2/042; A61F 2/50; A61B 5/040001; A61B 5/4076; A61B 5/4836; A61N 1/36003; A61N 1/36025; A61N 1/36082
USPC .......................................................... 607/45
See application file for complete search history.

(56) References Cited

U.S. PATENT DOCUMENTS 5,638,826 A 6/1997 Wolpaw et al.
7,058,445 B2 6/2006 Kemere et al.
(Continued)

OTHER PUBLICATIONS

Jones et al., "Impairment and Recovery of Ipsilateral Sensory-Motor Function Following Unilateral Cerebral Infarction," Brain 112(1): 113-132 (1989).
(Continued)

*Primary Examiner* — William J Levicky
*Assistant Examiner* — Minh Duc G Pham
(74) *Attorney, Agent, or Firm* — Armstrong Teasdale LLP

(57) ABSTRACT

A system for controlling a body part includes a number of sensing devices that sense signals from a hemisphere of a brain. A signal translating unit translates the signals into a command signal for controlling the body part, which is on a same side of the body as the hemisphere of the brain. A prosthetic device receives the command signal from the signal translating unit and manipulates the body part in response to the command signal.

17 Claims, 12 Drawing Sheets

Related U.S. Application Data continuation of application No. 12/133,919, filed on Jun. 5, 2008, now abandoned.

(60) Provisional application No. 60/933,433, filed on Jun. 5, 2007.

(51) Int. Cl.
| | | |
|---|---|---|
| *A61B 5/04* | (2006.01) | |
| *A61F 2/04* | (2013.01) | |
| *A61F 2/50* | (2006.01) | |
| *A61F 2/68* | (2006.01) | |
| *A61F 2/70* | (2006.01) | |
| *A61F 2/76* | (2006.01) | |
| *A61N 1/36* | (2006.01) | |
| *A61F 2/48* | (2006.01) | |

(52) U.S. Cl.
CPC ...... *A61N 1/36003* (2013.01); *A61N 1/36025* (2013.01); *A61N 1/36082* (2013.01)

(56) References Cited

U.S. PATENT DOCUMENTS

| | | |
|---|---|---|
| 7,120,486 B2 | 10/2006 | Leuthardt et al. |
| 7,826,894 B2 | 11/2010 | Musallam et al. |
| 2005/0131311 A1 | 6/2005 | Leuthardt et al. |
| 2006/0173259 A1 | 8/2006 | Flaherty et al. |
| 2007/0179534 A1* | 8/2007 | Firlik ............... A61B 5/16 607/3 |
| 2009/0221928 A1* | 9/2009 | Einav ............... A61B 5/0484 600/544 |
| 2010/0094154 A1 | 4/2010 | Schalk et al. |

OTHER PUBLICATIONS

Mehring et al., "Comparing information about arm movement direction in single channels of local and epicortical field potentials from monkey and human motor cortex", Journal of Physiology—Paris, 98(4-6): 498-506 (2004).

Porro et al., "Ipsilateral involvement of primary motor cortex during motor imagery", European Journal of Neuroscience, 12(8): 3059-3063 (2000).

European Search Report issued for Application No. 08780761.6 dated Jul. 2, 2013 (10 pages).

International Search Report Issued for PCT/US2008/065953, dated Oct. 1, 2008 (1 page).

\* cited by examiner

| Subject | Motor Action | Fingers Identified (#) | Fingers separable by cortical location | Number of fingers distinguishable between ipsilateral and contralateral fingers |
|---|---|---|---|---|
| 1 | Ipsilateral | 4 | 4 | 8 |
| | Contralateral | 5 | 5 | |
| 2 | Ipsilateral | 4 | 4 | 8 |
| | Contralateral | 4 | 4 | |

| Table 3: Summary of Online Control Data. The Anatomic and spectral feature utilized for control and their associated performance for each subject. |||||
|---|---|---|---|---|
| Subject | Hand Motor Action | Anatomic Location | Frequency (Hz) | Final Target Accuracy (%) |
| 1: Different location/ Different Frequency spectra | Ipsilateral | Primary Sensorimotor cortex | 25 | 96 |
| | Contralateral | Primary Sensorimotor cortex | 100 | 100 |
| 5: Same location/same frequency spectra | Ipsilateral | Primary Sensorimotor cortex | 100 | 70 |
| | Contralateral | Primary Sensorimotor cortex | 100 | 97 |
| 6: Same location/different frequency | Ipsilateral | Primary Sensorimotor cortex | 20 | 91 |

Figure 8

METHODS AND SYSTEMS FOR CONTROLLING BODY PARTS AND DEVICES USING IPSILATERAL MOTOR CORTEX AND MOTOR RELATED CORTEX

RELATED APPLICATION DATA

This application is a continuation application claiming priority from U.S. patent application Ser. No. 14/291,603 filed on May 30, 2014, which claims the benefit of U.S. patent application Ser. No. 12/133,919 filed on Jun. 5, 2008, which claims the benefit of U.S. Provisional Application No. 60/933,433, filed on Jun. 5, 2007. Each of these applications is incorporated herein by reference in their entirety.

FIELD OF THE INVENTION

The present invention relates, generally, to neuroprosthetics and, more particularly, to methods and systems for controlling body parts and devices using ipsilateral motor cortex and motor related cortex.

BACKGROUND OF THE INVENTION

In normal brain function, one side of the brain (a hemisphere) controls the opposite side of the body. Thus, the right brain (right cerebral hemisphere) controls the left side of the body and the left brain (left cerebral hemisphere) controls the right side of the body. As such, when an individual has a stroke on one side of the brain, the opposite side of the body is typically left paralyzed or weak.

This opposite side control of the body by the brain has dictated how conventional brain computer interfaces have been designed. Conventional methods and systems have used brain control devices that use signals from the brain that correlate with contralateral arm movements (i.e., decoding signals from the brain that control the arm and hand on the opposite side of the body) to control an external object such as a robotic arm. These methods have not used signals taken from a cerebral hemisphere (i.e., left) and used ipsilateral movements (i.e., left) as a signal for overt control.

Financial cost of lifetime care for U.S. subjects suffering from hemispheric stroke is typically prohibitive. Hemiparesis is one of the most common reasons for their disability, and it is often hand function that is impaired. Motor cortex ipsilateral control to the affected limb is thought to play a role in recovery, yet its role in controlling ipsilateral limb movement conventionally has not been well understood. Functional studies in both normal and stroke-recovered subjects have demonstrated regions of activation with ipsilateral hand movements that are distinct from those motor sites associated with contralateral hand movements. Conversely, some groups have found ipsilateral activation not to correlate, or worse, to be indicative of poorer outcome in hemiparetic patients or subjects. The conventional techniques used in these studies, however, possess limitations of either spatial or temporal resolution, prohibiting a more definitive understanding of cortical processing of ipsilateral hand movements.

Therefore, there is a need to remedy the problems noted above and others previously experienced for using signals taken from the same side of the brain (ipsilateral) which correspond to movements from the same side of the body and to achieve an overt device control.

SUMMARY OF THE INVENTION

The foregoing problems are solved and a technical advance is achieved by methods, systems and articles of manufacture consistent with the present invention, which provide neuroprosthetic controls of both sides of the body by using a single brain hemisphere.

In accordance with methods consistent with the present invention, a method for controlling a body part is provided. The method comprises: sensing a plurality of signals from a hemisphere of a brain; translating the sensed signals into a command signal for controlling the body part, which is on a same side of the body as the hemisphere of the brain; and manipulating the body part in response to the command signal.

In accordance with systems consistent with the present invention, a system for controlling a body part is provided. The system comprises: a plurality of sensing devices that sense signals from a hemisphere of a brain; a signal translating unit that translates the sensed signals into a command signal for controlling the body part, which is on a same side of the body as the hemisphere of the brain; and a device that receives the command signal from the signal unit and manipulates the body part in response to the command signal.

In accordance with articles of manufacture consistent with the present invention, there is provided a computer-readable medium containing a computer program adapted to cause a data processing system to execute a method for controlling a body part. The method comprises: sensing a plurality of signals from a hemisphere of a brain; translating the sensed signals into a command signal for controlling the body part, which is on a same side of the body as the hemisphere of the brain; and manipulating the body part in response to the command signal. The computer-readable medium may be, for example, a computer-readable storage medium such as a solid-state memory, magnetic memory such as a magnetic disk, optical memory such as an optical disk, or a computer-readable transmission medium, such as a modulated wave (such as radio frequency, audio frequency or optical frequency modulated waves) or a modulated downloadable bit stream that can be received by a computer via a wired or a wireless connection.

Other features of the invention will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The accompanying drawings, which are incorporated in and constitute a part of this specification, illustrate an implementation of the present invention and, together with the description, serve to explain the advantages and principles of the invention. In the drawings:

FIG. 8 is a table illustrating a comparison of accuracy of controls achieved from signals derived from ipsilateral and contralateral motor movements in accordance with the present invention;

DETAILED DESCRIPTION OF THE PREFERRED EMBODIMENTS

Figure 1:
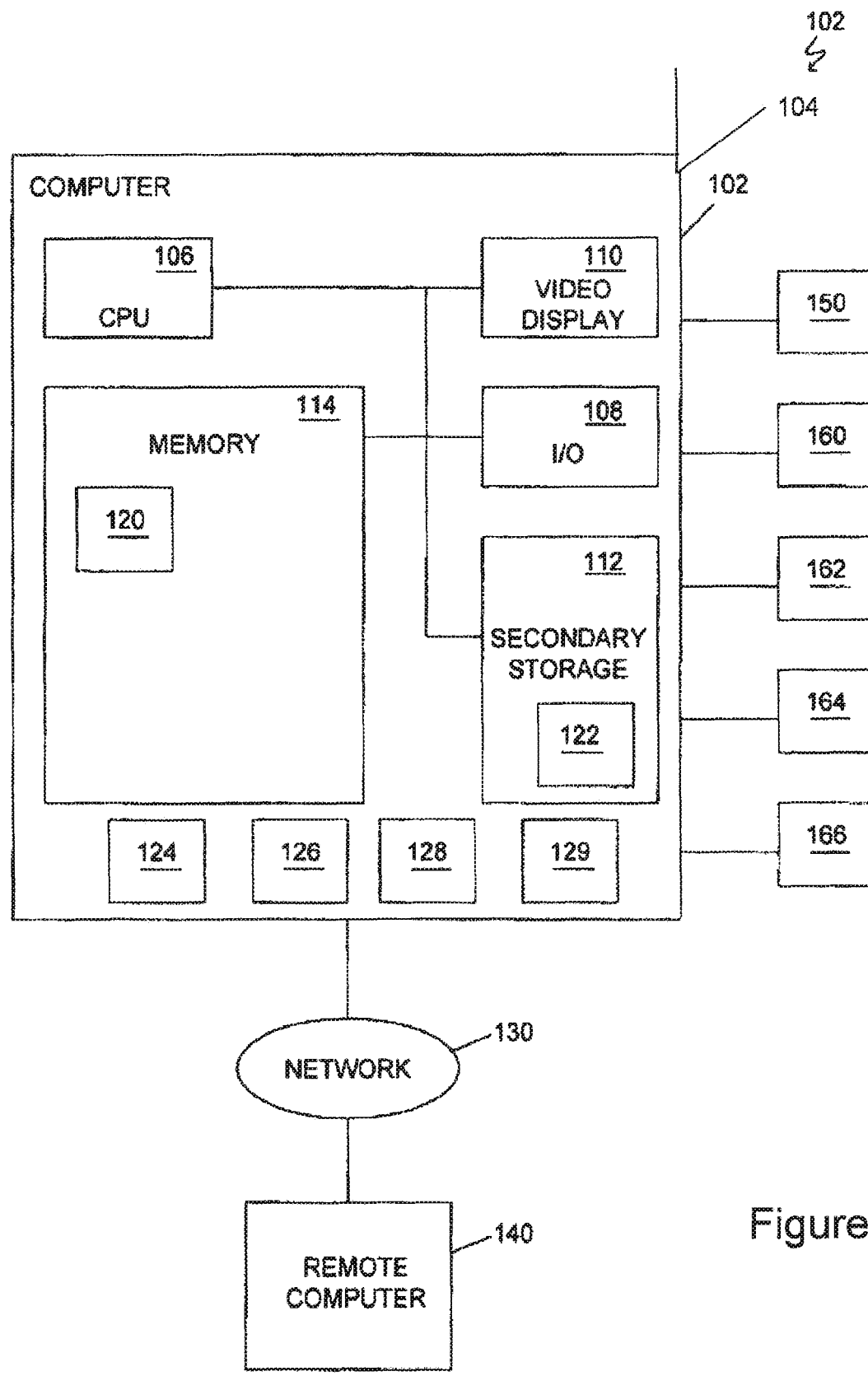
FIG. 1 is a block diagram illustrating one embodiment of a data processing system that includes an electrocorticographic hemispheric brain computer interface (BCI) used for bisomatic control in accordance with the present invention.

Reference will now be made in detail to an implementation consistent with the present invention as illustrated in the accompanying drawings. Wherever possible, the same reference numbers will be used throughout the drawings and the following description to refer to the same or like parts. As would be understood to one of ordinary skill in the art, certain components or elements are not shown in the figures or specifically noted herein to avoid obscuring the invention.

Conventional brain computer interfaces (BCIs) have typically offered minimal benefit to subjects with motor impairment due to, for example, unilateral stroke because conventional platforms or systems rely on signals derived from the contralateral motor cortex, which is the same region injured by the stroke or other impairment. For a BCI to assist a hemiparetic subject, the unaffected cortex ipsilateral to the affected limb (opposite the side of the stroke) needs to be utilized. The affected limb or body part may be motor-impaired due to, for example, a unilateral stroke, a spinal cord injury, a neuromuscular disorder, a traumatic brain injury, a limb amputation, and peripheral nerve injury. To do so, an expanded understanding of how motor cortex participates in processing ipsilateral limb movements is essential.

Methods, systems and articles of manufacture consistent with the present invention provide an implantable BCI that can control, for example, a paretic hand for the subject with a motor impairment, such as a unilateral stroke, by utilizing the cortical signals from the unaffected hemisphere. This is achieved by identifying distinct and independent electrophysiological features from, for example, the motor cortex associated with ipsilateral hand movements and utilizing these features for external device control and defining dynamic changes with ongoing performance. The cortical electrophysiologic changes associated with ipsilateral movements, such as hand movements, are distinct and these unique ipsilateral changes can support an independent thought-driven device control. The cortical signals may be sensed, for example, from one or more of the primary motor cortex, the premotor cortex, the frontal lobe, the parietal lobe, the temporal lobe, and occipital lobe of the brain, and the like.

The cortical signals may be obtained from one or more of electrocorticographic (ECoG) signals, electroencephalography (EEG) signals, local field potentials, single neuron signals, (MEG) magnetoencephalography signals, mu rhythm signals, beta rhythm signals, low gamma rhythm signals, high gamma rhythm signals, and the like. The ECoG, EEG, local field potentials, and MEG signals may include at least one of the following: mu rhythm signals, beta rhythm signals, low gamma rhythm signals, and high gamma rhythm signals. The signal data is converted into the frequency domain and spectral changes are identified with regards to frequency, location, and timing. Features specific to ipsilateral motor control, such as hand movements, may be utilized to control a device, such as a cursor on a screen in real time (both in isolation and in parallel with contralateral hand tasks). This approach is innovative because it may capitalize on the high signal resolution of ECoG, for example, to reveal aspects of cortical motor processing not appreciable by noninvasive means.

FIG. 1 is a block diagram that depicts an embodiment of a data processing system 102 consistent with the present invention. The data processing system 102 includes a computing unit 104 configured to receive sensor data or signals, translate or convert the received data, and communicate the translated data to control a device (not shown). The controlled device may be any type of device that can be controlled by an external signal, such as but not limited to a robotic device, a transportation device, a prosthetic control device, and the like. In an illustrative example, the prosthetic control device may be an external robotic assist device. The prosthetic control device may utilize, for example, one or more of external nerve stimulators, external muscle stimulators, internally implanted nerve stimulators, and internally implanted muscle stimulators. The prosthetic control device may be utilized, for example, for hand controls, arm controls, leg controls, foot controls, bladder controls, and the like. In an illustrative example, the prosthetic control device may be a prosthetic limb for an amputee.

Computing unit 104 comprises a central processing unit (CPU) 106, an input output I/O unit 108, a display device 110, a secondary storage device 112, and a memory 114. Computing unit 104 may further comprise standard input devices such as a keyboard, a mouse, a digitizer, or a speech processing unit (each not illustrated).

In the illustrative example, computing unit 104 communicates via a network 130, such as a LAN or the Internet, with a remote computing unit 140. Remote computing unit 140 provides remote storage for computing unit 104. The number of computing units and the network configuration shown in FIG. 1 are merely illustrative. One of ordinary skill in the art will appreciate that the data processing system 102 may include a different number of computers and networks.

Memory 114 includes a program 120 having instructions for receiving sensor data, and converting the received data into controlling data to control a device 150, such as a prosthetic device. Sensor data can be received from a variety of sources. In the illustrative example, sensor data is received from ECoG sensors 160, the prosthetic device 150, data gloves 162, a joystick 164, and a microphone 166. These devices are merely illustrative. Additional or alternative devices may be implemented. Data may be received via data interface devices 124, 126, 128, and 129 and stored in a file 122 in the secondary storage 112. In an embodiment, the data interface devices comprise Guger Technologies optically isolated g.USBamp amplifiers, or the like. AdTech medical splitter cables are used, for example, to connect to clinical monitoring cables.

The data gloves (1 right and 1 left) are, for example, 5DT 14 Ultra Data gloves. These gloves interface with the computing unit 104 via USB connections and allow for direct measurements of finger movements to be recorded and used in data processing. These illustrative gloves have the capability to measure finger flexion (2 sensors per finger) as well as finger abduction. This information can be used to determine the timing of actual movements as well as their duration and velocity. These gloves are made of stretch Lycra that is well tolerated by users or subjects and configured to fit many hand sizes.

The illustrative computing unit 104 is, for example, a Dell Precision 690 with Quad Core Intel Xeon Processor X5355 (2.66 GHz, 4 MB RAM, 300 GB storage). Further, the illustrative computer may be a mobile data collection computing unit that may be moved to or with the subject.

The remote computing unit 140 is, for example, a Dell PowerEdge 2950 server (Quad Core Intel Xeon E5345, 2.33 GHz, 1333 MHz, 16 GB RAM, 1.5 TB Hard Drive with a Dell/EMC SAN Disk Enclosure). This computer set-up can provide storage of large quantities of data. An average subject may easily generate 100 gigabytes of data.

The illustrative data interfaces are, for example, Guger technologies g.USBamp Amplifiers. These FDA-approved amplifiers are optically isolated amplifiers that are approved for use with invasively monitored subjects. The optical isolation prevents electrical discharge from being passed from the computer system 102 to the subjects or users. Additionally, these amplifiers are compatible with BC1200 software. Each amplifier is capable of recording 16 channels (i.e., 16 invasively placed electrodes).

Forty percent of all stroke sufferers are left with a permanent hemiparesis; most commonly, this involves an acute decrement in hand function that shows some recovery for several months. The undamaged hemisphere that is ipsilateral to the affected limb is thought to play a role in this stroke recovery. Relatedly, functional imaging studies have demonstrated that motor cortex is involved in ipsilateral hand and limb movements in both normal and stroke-recovered human subjects. Recent studies suggest that sites associated with ipsilateral motor movements are anatomically and temporally distinct from the locations and timing associated with contralateral limb movements.

There are electrophysiologic features that distinguish and encode cortical processing for ipsilateral and contralateral movement, such as hand movements. One strategy in stroke rehabilitation is to aid the ipsilateral cortex to take over function of the damaged contralateral hemisphere. Methods, systems, and articles of manufacture consistent with the present invention accomplishing this through the use of the system's brain computer interface (BCI) that converts brain signals directly to machine device commands without the need for the brain's normal output pathways of peripheral nerves and muscles.

In another embodiment, the data processing system 102 is implemented as an implantable brain computer interface (BCI) that can control, for example, a paretic hand for a subject with unilateral stroke by utilizing the cortical signals ipsilateral to the affected limb (i.e., signals taken from the surface of the unaffected hemisphere). The BCI uses the cortical electrophysiologic changes associated with ipsilateral hand movements that are distinct and these unique ipsilateral changes support independent thought-driven device control.

Ipsilateral hand and finger movements, for example, produce electrocorticographic changes that have distinct cortical locations, are earlier in temporal onset, and associated with lower frequency spectral alterations when compared against contralateral hand movements. Localization of this effect is different between the right and left hemisphere. The unique spatial and spectral electrophysiologic features associated with ipsilateral hand movements can be effectively utilized by a human subject to control an external device in accordance with the present invention. This is accomplished in isolation (ipsilateral hand movement alone), or in parallel with the physiologic operation of the contralateral limb. With ongoing control, these brain signals will demonstrate dynamic plasticity to improve performance.

The signals, such as ECoG signals, associated with ipsilateral movements, such as hand movements, have anatomically distinct regions, occur earlier, and show lower frequency predominance when compared to contralateral body part movements. These distinct signal features may be utilized, for example, to achieve control of an external device, such as a cursor on a computer screen.

The processing system 102 is configured to capitalize on the unique spatial, temporal, and signal advantages of the signals, such as ECoG, to reveal aspects of cortical motor processing not possible by noninvasive approaches. These distinct features are separable from the physiologic changes associated with contralateral movements and can be utilized for external device control. These results provide a substantive positive impact in that they provide neuroprosthetic strategies to ameliorate motor impairment, such as stroke-induced hemiparesis. This alters conventional perceptions of stroke recovery from one of watchful rehabilitation to a more directed approach of restoring function.

In an illustrative example, electrical activity taken directly from the surface of the brain, or ECoG, provides a beneficial source for integrated information that leads to a significant paradigm shift in understanding brain function compared to conventional approaches. ECoG has a desirable signal-to-noise ratio, millisecond timescales, millimeter spatial resolution, and a broad frequency bandwidth that in combination are not available with other techniques. Through experimentation, the inventors have identified that ECoG is effective as a signal in motor brain mapping, neuroprosthetic applications, and its ability to convey very specific information regarding motor intentions.

The BCI consistent with the present invention does not depend on the brain's normal output pathways of peripheral nerves and muscles. The illustrative BCI decodes human intent from brain activity alone in order to create an alternate communication and control channel for people with motor impairments.

This brain-derived control is predicated on an understanding of cortical physiology as it pertains to motor function. Research has determined that neurons in the motor cortex show directional tuning and, when taken as a population, can predict direction and speed of arm movements in monkey models. Subsequently, these findings were translated to substantial levels of brain-derived control in monkey models and preliminary human clinical trials. In another example of analyzing electroencephalography (EEG), changes in amplitudes in sensorimotor rhythms associated with motor movement were described. As a result, these EEG signals have been used to achieve basic levels of control in humans with amyotrophic lateral sclerosis (ALS) and spinal cord injury.

However, these conventional approaches do not assist subjects suffering from hemispheric stroke. The conventional methods are based on functioning motor cortex capable of controlling the contralateral limbs. This situation does not exist in unilateral stroke. For a BCI to assist a hemiparetic subject, the implant must utilize unaffected cortex ipsilateral to the affected limb (opposite the side of the stroke). To do so, an understanding of how the motor cortex participates in processing ipsilateral arm and hand movements must be used.

Conventional Approaches and Research

The notion that motor cortex plays a role in ipsilateral body movements was determined when 15% of corticospinal neurons did not decussate in cats. Further studies in single neuron recordings in monkey models extended this understanding to include ipsilateral hand and finger function. For example, some studies demonstrated that a small percentage of primary motor cortical neurons showed increased activity with ipsilateral hand movements. This primary motor cortical site was found to be anatomically distinct from contralateral hand sites and, when stimulated, produced ipsilateral hand movements. Additionally, a larger subset of premotor neurons was found to demonstrate more robust activations with cues to initiate movement during both ipsilateral and contralateral movements than with primary motor sites.

Additional findings demonstrated that in motor and supplemental motor cortex there was single neuronal activity associated with bilateral movements that was distinct from unimanual movements. These findings led to the conclusion that motor and motor-associated cortex share in control of both contralateral and ipsilateral limb and hand movements.

The evidence cited above has led to further investigation in humans. Clinical studies have demonstrated that injury to motor cortex still has functional impact on the ipsilateral "unaffected" limb. Imaging studies with functional magnetic resonance imaging (fMRI), positron emission tomography (PET) and single photon emission computed tomography (SPECT), have further confirmed in normal human subjects that various levels of ipsilateral motor and motor-associated cortex are active with ipsilateral hand movements. Other findings have extended this concept by showing these regions to be anatomically distinct; located anterior, ventral, and lateral to the activations induced by contralateral hand movements.

Additionally, this activation appears to be more closely associated with hand movements that are more complex or lengthy in sequence duration. The hemispheric distribution has also been found to be asymmetric, favoring the left hemisphere in righthanded subjects. These findings of distinct anatomic position, association with increased manual complexity, and hemispheric dominance in normal human subjects have been further corroborated by magnetoencephalography (MEG) and transcranial magnetic stimulation (TMS).

The manner that motor cortex is involved with ipsilateral motor movements in humans, however, has not been well defined; moreover, the extant literature has conflicting findings. Utilizing fMRI, it was determined that the time course analysis of complex ipsilateral finger movements support the premise that primary motor cortex may participate in execution of complex movements rather than their planning. This, however, is in contradiction to findings which demonstrated ipsilateral premotor areas having MEG dipole peak latencies that significantly preceded contralateral M1 sensorimotor cortex in performing unilateral finger movements. These findings were posited to support more of a motor planning role in ipsilateral finger actions. Still another and opposite perspective reported decreased fMRI bold signals in ipsilateral motor cortex with unilateral hand movements. This negative of baseline change intensified with increased duration of movement. The authors postulated this to represent transcallosal inhibition. To date, it has not been conventionally resolved whether these changing activations found on functional imaging or MEG represent motor planning, motor execution, or epiphenomenon related to transcallosal inhibition.

Definitive electrophysiologic studies in humans to parse out the role that motor cortex plays in ipsilateral hand movements and to define the manner in which it is physiologically encoded have been limited. This is due either to the limitations of the modality or of the study design. To date, the majority of conventional electrophysiologic studies of human brain function have utilized EEG. Brain activity has been assessed by either alterations in field potentials or by the spectral changes of oscillating brain activity (AKA sensorimotor rhythms). Ipsilateral hand movements have been shown to induce alteration in cortical potentials prior to movement; this is referred to as "premotor positivity." Spectral analyses of EEG signals have demonstrated bilateral low frequency responses with various finger and hand movements. Additionally, a more robust activation in left over right sensorimotor cortex in preparation and performance of simple finger movements was determined. The EEG modality, however, is limited by poor spatial resolution (3 cm) and by spectral bandwidth (frequencies under 40 Hz). This ultimately limits the precision with which it can describe the anatomy and signal characteristics of the cortical electrophysiology underlying ipsilateral motor processing.

Ipsilateral Control of Devices

Unlike conventional approaches, methods, systems, and articles of manufacture consistent with the present invention provide neuroprosthetic controls of both sides of the body by using a single brain hemisphere. A plurality of signals is sensed from a hemisphere of the brain. In an illustrative example, Electrocorticography (ECoG), or signal recorded from the surface of the brain is employed. The ECoG signal is much more robust compared to EEG signal: its magnitude is typically five times larger, its spatial resolution as it relates to independent signals is much greater (0.125 versus 3.0 cm for EEG), and its frequency bandwidth is significantly higher (0-500 Hz versus 0-40 Hz for EEG). When analyzed on a functional level, different frequency bandwidths carry highly specific and anatomically focal information about cortical processing. The lower frequencies bands known as mu frequencies (8-12 Hz) and beta frequencies (18-26 Hz) may be produced by thalamocortical circuits and often decrease in amplitude in association with actual or imagined movements. Higher frequencies (>30 Hz), or gamma rhythms, may be produced by smaller cortical assemblies and may be associated with numerous aspects of speech and motor function. No conventional studies or systems have utilized these ECoG spectral features to analyze cortical processing of ipsilateral movements.

The same advantages in spatial and signal resolution that make the use of electrocorticography a superb method for brain mapping also confer similar advantages for neuroprosthetic application. In experiments, the present inventors have demonstrated the first use of ECoG in closed-loop control in one-dimensional and two-dimensional controls. Both were accomplished with minimal training requirements. Additional experiments demonstrated that specific frequency alterations encode very specific information about motor actions (e.g., direction of joystick movement). The present inventors further demonstrated that ECoG control using signals from the epidural space was also possible. Taken together, these studies show the ECoG signal to carry a high level of specific cortical information, and these signals can allow a user to gain control rapidly and effectively.

Thus, the inventors have demonstrated that the cortical electrophysiologic changes associated with ipsilateral movements, such as hand movements, are distinct and that these unique ipsilateral changes can support independent thought-driven device control. Through experimentation, the inventors arrived at these demonstrations building on initial studies that showed the following individual understandings: (1) there are distinct premotor anterior/lateral anatomic locations found in both animal models and in human functional imaging studies associated with ipsilateral hand and finger movements, (2) there is earlier temporal onset of brain signal alteration measured by the "premotor positivity" in EEG/ECoG and the anterior localized dipole moments measured with MEG when compared to signals elicited by contralateral hand movements, (3) there is a bilateral representation of mu and beta rhythms with both real and imagined motor movements measured with EEG and ECoG, and (4) the high level of motor information and rapid and effective control that can be derived from the ECoG signal.

Methods and systems consistent with the present invention satisfy the substantial need to integrate the anatomic, temporal, and signal aspects of the cortical physiology involved with processing ipsilateral hand movements and provide a utility for BCI application. This integration is accomplished through the use of electrocorticography, for example. This allows for a BCI that achieves "bisomatic" control—a neuroprosthetic that can enable a single hemisphere to facilitate control of both sides of the body.

Preliminary Studies

Through research, it has been determined that for both ipsilateral gross hand movements and finer hand movements (i.e., finger movements) there are distinct anatomic sites of cortical activity that are more highly represented in the lower frequencies. These findings underscore the high fidelity of ECoG at discerning information from cortex (from gross hand movements to individual finger movements) but also are important when considering the type of hand prosthetic that may be used. Ipsilateral activity occurs earlier than activity associated with contralateral movements. These separable timescales support a more motor planning role and further distinguish ipsilateral and contralateral processing. The low frequency spectra associated with ipsilateral movements conveys specific information about the given motor movement. A different anatomic localization exists between the right and left hemisphere for ipsilateral motor processing. Beyond demonstrating that a distinct ipsilateral cortical motor physiology exists, these features may be utilized to achieve independent real-time device control in time scales that make this approach feasible for translational application. To utilize brain signals unique to ipsilateral hand movements for device control and to define dynamic changes with ongoing performance, it has been demonstrated that a subset of subjects achieved control of a computer cursor using signals derived from overt ipsilateral hand movements, and that improvement in performance are associated with ongoing changes in brain signal. These findings show human subjects gaining control substantially rapidly and, through ongoing feedback, they may alter their brain signals to optimize device performance.

The subjects in this study were six subjects (ages 11-50 years) with intractable epilepsy who underwent temporary placement of intracranial electrode arrays to localize seizure foci prior to surgical resection. They included three men (Subjects 1, 2, and 3) and three women (Subjects 4, 5, and 6). All subjects had normal levels of cognitive function. Two subjects had right hemispheric 8×8 grid electrodes, two subjects had left hemispheric 8×8 grid electrodes, and two had bihemispheric strip electrodes (1×8 electrode array). Each subject studied was in a sitting position (semirecumbent), approximately 75 cm from a video screen (setup shown in FIG. 1). In all experiments, ECoG was recorded from up to 64 electrodes from a combination of grids and strips using the general purpose BCI system BC12000 (Schalk, 2004). All electrodes were referenced to an inactive intracranial electrode, amplified, bandpass filtered (0.15-500 Hz), digitized at 1200 Hz, and stored. The amount of data obtained varied from subject to subject and depended on the subject's physical state and willingness to continue. The subjects performed various hand, finger, and joystick tasks with their right and left hands (described below). The time-series ECoG data was converted into the frequency domain using an autoregressive model. Spectral amplitudes were calculated between 0 and 200 Hz in 2-Hz bins. Those electrodes and frequency bins with the most significant task-related amplitude changes (i.e., the highest values of r2) were identified. In a subset of subjects (3), closed-loop BCI experiments were attempted with the subject receiving online feedback that consisted of one-dimensional vertical cursor movement controlled by ECoG features that had shown correlation with tasks during the various screening procedures.

Figures 2A, 2B:
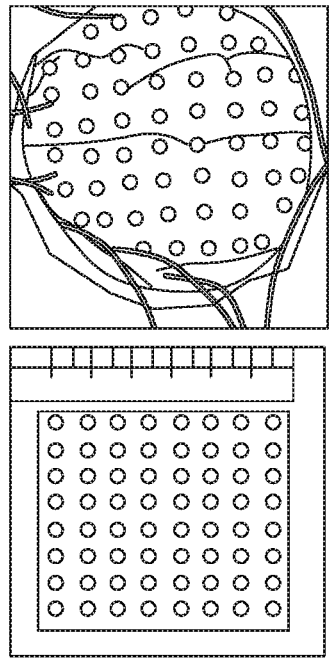
FIG. 2A illustrates an embodiment of an electrode grid used on a subject for collecting cerebral signals in accordance with the present invention.
FIG. 2B illustrates the electrode grid of FIG. 2A placed over the sensorimotor cortex of the subject's head in accordance with the present invention.
Figure 2D:
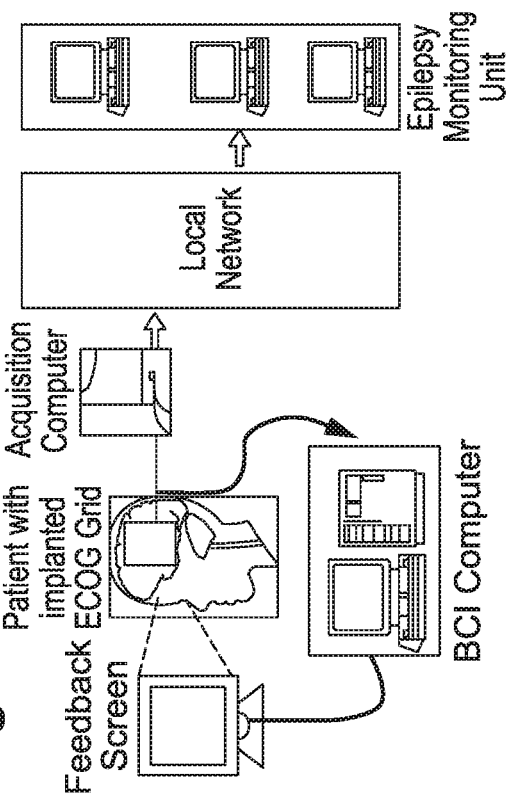
FIG. 2D is a schematic diagram of an embodiment of an electrocorticographic (ECoG) BCI system in accordance with the present invention.
Figure 2C:
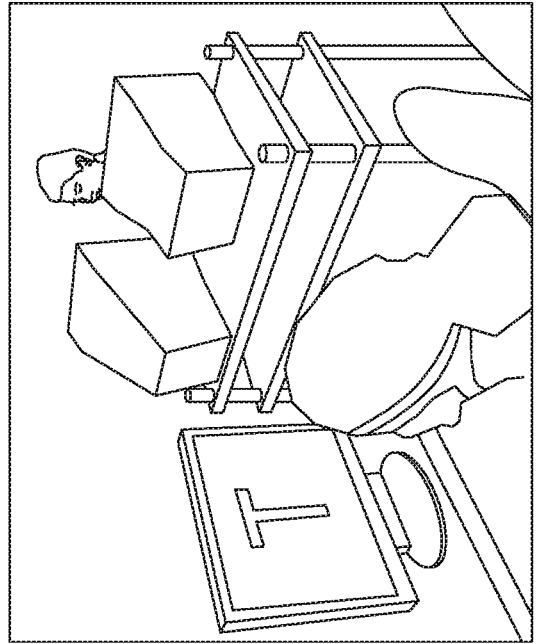
FIG. 2C illustrates the subject connected to the BCI of FIG. 1 in accordance with the present invention.

FIGS. 2A-D show the illustrative system used during the preliminary study. FIG. 2A shows the 64-electrode grid that is 8×8 cm in size. FIG. 2B shows an intraoperative picture of the grid placed over sensorimotor cortex. FIG. 2C shows a picture of the subject involved in the BCI operation. Notable elements are the feedback screen in front of the subject (*) and the BCI computer (**). FIG. 2D is a schematic diagram of ECoG BCI System. Once the subject had the subdural grid surgically implanted for purposes of seizure monitoring, the ECoG signal was routed to the computer. This signal was then sent to the network for which the signal tracings may be viewed for clinical purposes. For the purpose of BCI operation, the signal is split directly from the subject (A). This signal is then sent to the BCI computer, where the raw signal was analyzed, stored, and used for online control. In this example, the device command is controlling the movement of a cursor on the feedback screen.

Ipsilateral hand and finger movements, for example, produce electrocorticographic changes that have distinct cortical locations, are earlier in temporal onset, and associated with lower frequency spectral alterations when compared against contralateral hand movements. Localization of this effect is different between the right and left hemisphere.

All subjects performed an ipsilateral and contralateral hand motor task. This consisted of the subject participating for a minimum of six minutes performing repetitive three-second hand tasks consisting of opening and closing the right or left hand on cue. Each hand task was interspersed by a rest period of equal time. The time series ECoG data was converted into the frequency domain and each hand action was compared against rest. All subjects showed distinct electrodes sites and frequency spectra that distinguished between the ipsilateral and contralateral hand movement. As can be seen from the data shown in FIGS. 3A and 3B, ipsilateral hand movements produced spectral power changes that are lower in frequency when compared against contralateral hand movements and have anatomically distinct sites not present with contralateral hand movements.

Figure 3A:
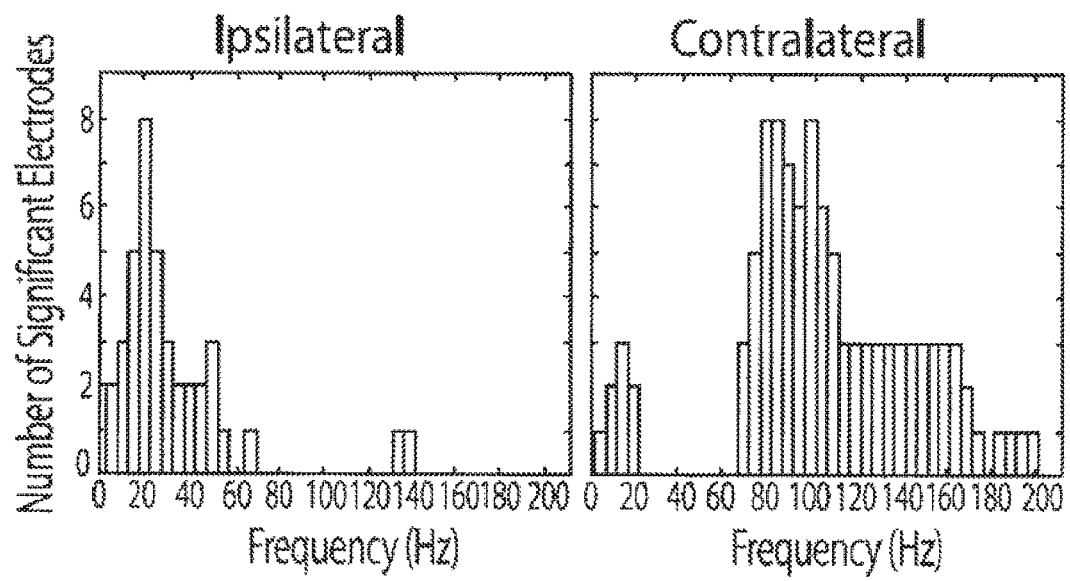
FIG. 3A illustrates two bar histograms in which a number of electrodes sensing significant cortical activity are plotted against frequency for ipsilateral and contralateral hand movements in accordance with the present invention.
Figure 3B:
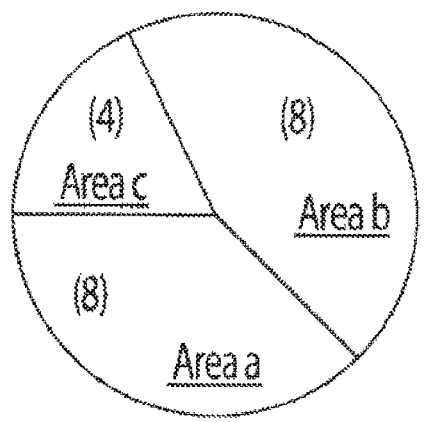
FIG. 3B is a pie chart illustrating the number of anatomic locations that show significant changes in activity for ipsilateral and contralateral hand movements in accordance with the present invention.

FIG. 3A illustrates two bar histograms in which the number of electrodes demonstrating significant cortical activity (spectral power changes with p-value<0.001) are plotted against frequency for ipsilateral and contralateral hand movements. Ipsilateral hand movements are predominantly represented in lower frequencies (average 32.8 Hz, SD+−14.4) compared to the higher frequency distribution associated with contralateral hand movements (average 106.7 Hz, SD+−20.8). FIG. 3B compares the number of anatomic locations that showed significant changes in activity (electrodes that show spectral power changes with p-values <0.001) for ipsilateral and contralateral hand movements. The pie chart shows there are an equal number of cortical locations which are distinct to ipsilateral and contralateral hand movements (eight sites each). Additionally, there are four sites that demonstrate an overlap. In these sites ipsilateral and contralateral movements demonstrate different average frequency spectra (ipsilateral movements 23.6 Hz, SD+−5.8 and contralateral movements 93.5 Hz, SD+1-24). Collectively, this data exhibits that there are distinct frequency spectra and cortical sites that distinguish ipsilateral hand movements from contralateral hand movements.

FIG. 3A shows that the number of electrodes that show significant power change (p-value<0.001) at a given frequency for ipsilateral and contralateral hand movements across all subjects with intracranial grid arrays. Ipsilateral hand movements are represented in a lower frequency range than that associated with contralateral hand movements.

FIG. 3B illustrates the number of locations identified with statistically significant power change (across all frequencies) that correlated with ipsilateral and contralateral hand movements. The number of sites that showed significant activity with ipsilateral hand movements (8) are in Area a, with contralateral hand movements (8) are in Area b, and locations that shared with both ipsilateral and contralateral hand movements (4) are noted in Area c. This data shows that there are sites for ipsilateral motor movements that are distinct from contralateral hand movements.

These figures represent data taken from all the subjects with intracranial grid arrays (Subjects 1 2, 3, and 6). The subjects performed three-second hand tasks consisting of opening and closing the right hand or the left hand on cue. Each hand task was interspersed by a rest period of equal time. The timeseries ECoG data was converted into the frequency domain using an autoregressive model in which each hand action was compared against rest. For each electrode, the amplitude changes at each 5 Hz frequency bin were correlated with each hand task by measuring the coefficient of determination values, or r2. An r2 value greater than 0.07 which has a p-value<0.001 is considered significant. Those electrodes found to be statistically significant were then plotted against frequency and also identified with regard to whether they were significant with ipsilateral or contralateral hand movements alone or in combination.

Distinguishing Individual Ipsilateral Finger Movements

Figures 4A, 4B:
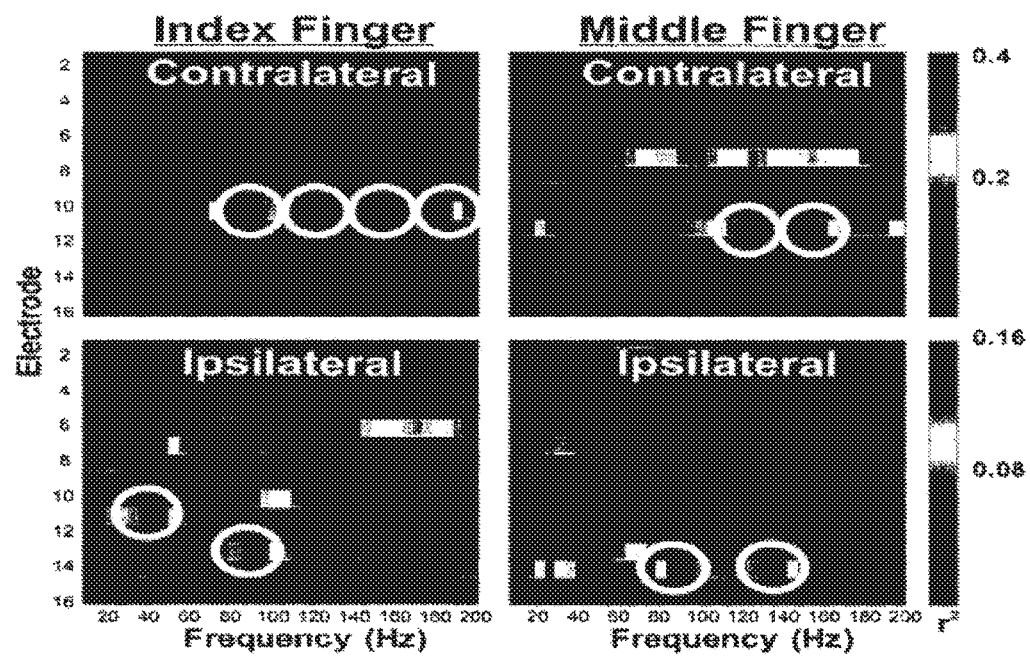
FIG. 4A shows images illustrating finger movements distinguished by differential cortical locations and frequency power alterations in accordance with the present invention.
FIG. 4B is a table illustrating the number of identified fingers for a couple of subjects for both ipsilateral and contralateral motor actions in accordance with the present invention.

To further define the level of resolution that electrocorticography can distinguish in the finer aspects of ipsilateral hand processing, namely individual finger movements, Subjects 1 and 2 were engaged to perform individual finger tasks consisting of tapping each individual finger on cue. The time-series ECoG data was converted into the frequency domain for each finger movement and was compared against rest. From the results shown in the table of FIG. 4B, ipsilateral finger movements were considered to be separable by the site of cortical activity and by the associated frequency bands that show significant power changes with finger movement. Additionally, for each subject the same finger of either hand could also be distinguished. Data from Subject 1 is shown in FIG. 4A, in which four feature plots are shown for contralateral index and middle finger movement (top row) and ipsilateral index and middle finger movement (bottom row). In each feature plot, frequency is plotted against anatomic location (electrode site). The shade change indicates the correlation of power change that occurs at that frequency bin with the active task when compared against rest (measured in r2). The figure illustrates that the index and middle fingers are separable by the distinct location and frequency power change for both the ipsilateral and contralateral conditions. Additionally, ipsilateral fingers can not only be separated from the other complementary finger, but from all other fingers. Also of note, the ipsilateral finger movements, when compared to their contralateral finger, have a significant portion of their unique spectral features in the lower frequencies (below 30 Hz). In this pilot study, 8 of 10 fingers were distinguished for the two subjects tested. This data is summarized in FIG. 4B. These findings demonstrate that the methodology is able to achieve a high level of resolution in distinguishing finer motor movements not discernable with other noninvasive modalities in humans. Moreover, the data processing system 102 is able to determine that the signals associated with ipsilateral motor movements reflect specific manual actions (e.g., finger movement) rather than just representing broad non-specific changes.

The table in FIG. 4B is a summary of the data taken from Subjects 1 and 2, who participated in cue initiated individual finger movements. In both subjects, eight of ten fingers were separable for a given hand and from all fingers from either hand. Ipsilateral and contralateral finger movements which demonstrated significant power changes (p<0.001) were identified (third column). For a given hand, the significant electrode location patterns were compared to identify if those location patterns matched with another finger movement induced electrode location pattern (ipsilateral index finger showed significant changes in electrodes 6, 7, 10, 11, and 13 versus ipsilateral middle finger, which showed electrode activation in electrodes 1, 7, 13, and 14). If they did not, they were considered separable for the given hand. The number of fingers separable for the ipsilateral and contralateral hand is shown in the fourth column. The electrode location patterns were then compared between hands (e.g., ipsilateral index finger versus all other nine fingers). If the given finger did not match any electrode location pattern of another finger, it was considered separable. The number of fingers separable from all other fingers is shown in the fifth column.

FIG. 4A shows the distinguishing finger movements by differential cortical locations and frequency power alterations. The data shows that index finger and middle finger movements demonstrate distinct locations (electrode, y axis) and frequency bands (x-axis) associated with the given finger, as indicated by circled areas in FIG. 4A. This is demonstrated for both ipsilateral and contralateral finger movements. The same finger movement is different depending on whether it is ipsilateral or contralateral. Additionally, ipsilateral finger movements have a more predominant lower frequency representation than their same contralateral finger movements. FIG. 4A represents data taken from Subject 1. Subject 1 performed three-second finger tasks consisting of tapping each individual finger on cue. The finger tasks were interspersed by a rest period of equal time. The time-series ECoG data was converted into the frequency domain using an autoregressive model in which each finger activity was compared against rest. The electrodes were plotted against the frequency measured in 5 Hz Bins. The color was scaled by the relative level of correlation that amplitude change occurred with the respective finger task (measured by coefficient of determination values, or r2). An r2 value greater than 0.07 represents a p-value that is less than 0.001. The left column represents index finger movements; the right column represents middle finger movements. The top row indicates that these movements were contralateral, and the bottom row indicates that these movements were ipsilateral.

Cortical Activity Occurs Earlier With Ipsilateral Hand Movements

Figure 5A:
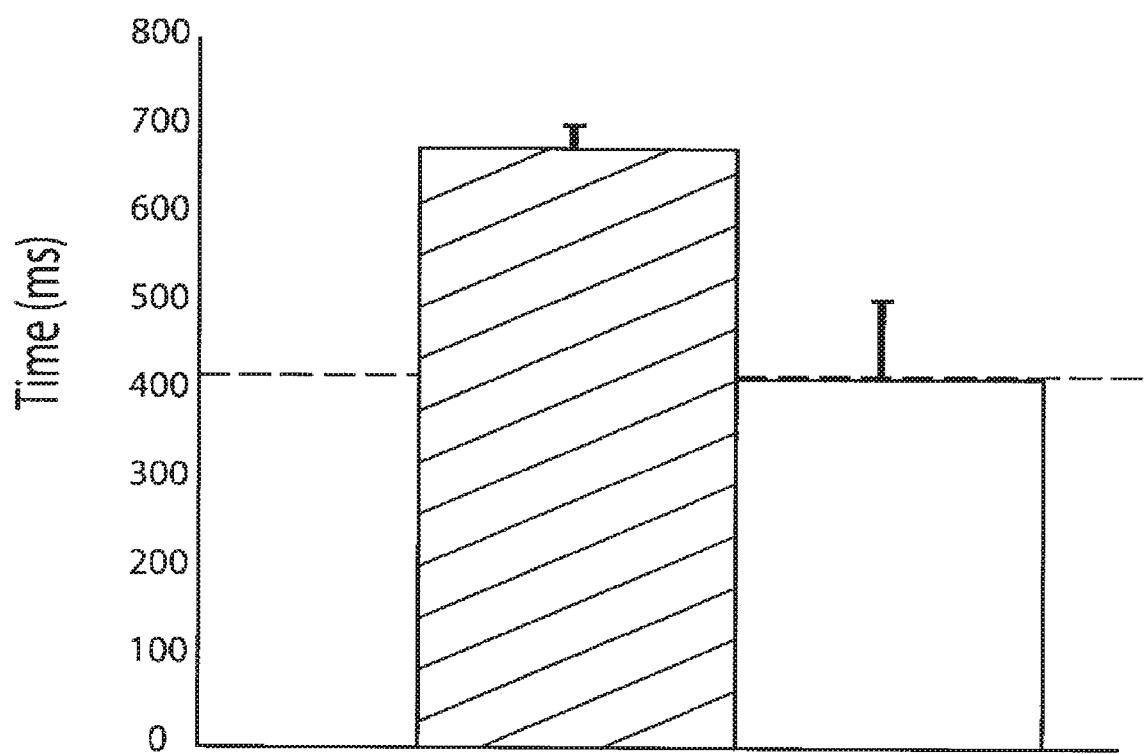
FIG. 5A shows a bar histogram that illustrates peak times of signal correlation with the active condition averaged across three subjects in accordance with the present invention.
Figure 5B:
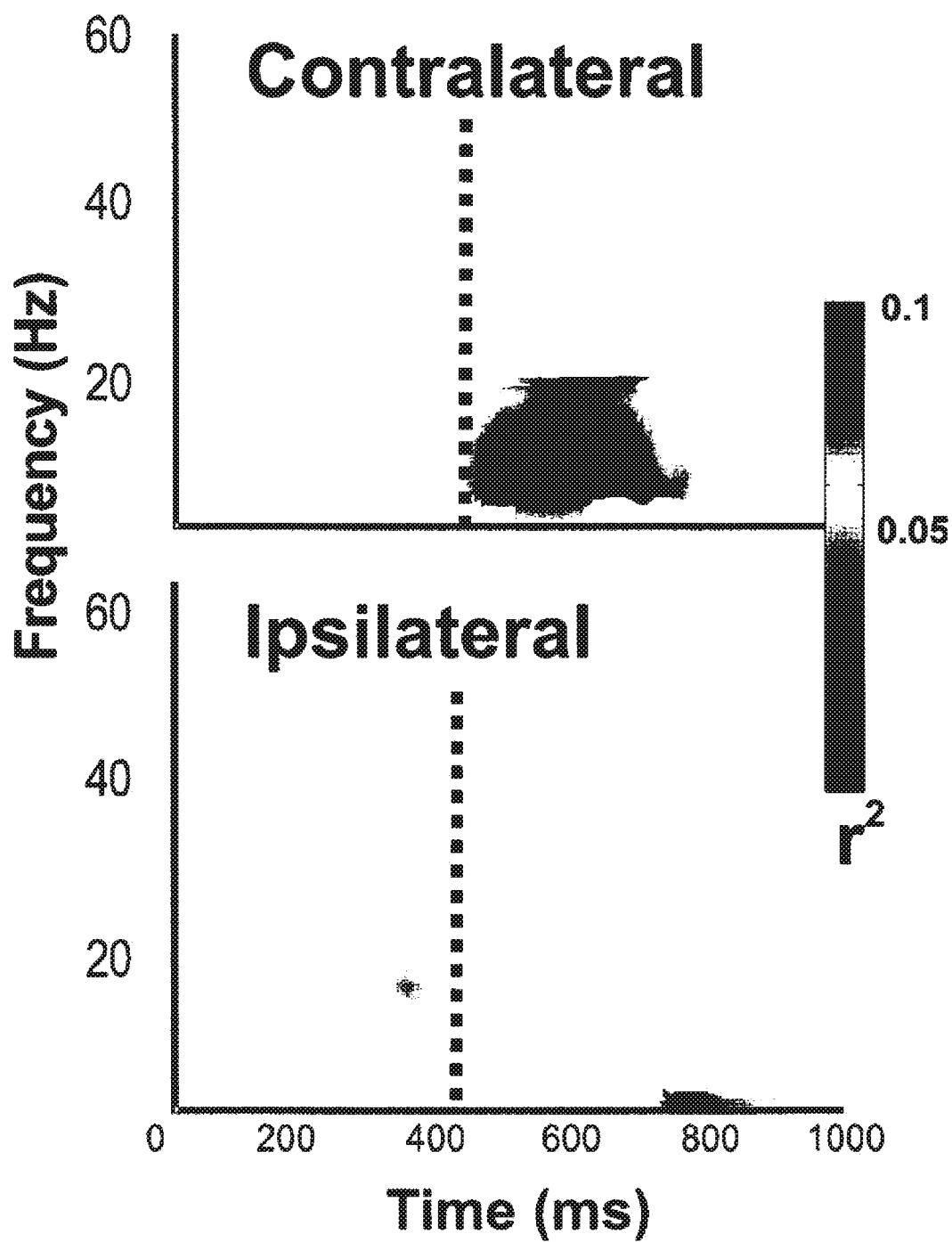
FIG. 5B shows two graphs that data comparing the timing of the earliest significant electrode for contralateral movement and for ipsilateral movement for a subject in accordance with the present invention.

To further define the unique aspects of ipsilateral motor processing, three subjects (1, 3, and 6) performed cue-directed hand-controlled joystick center-out tasks with both the right hand and left hand. This arrangement allowed to precisely determine the timing of cue presentation, motor movement, and associated spectra changes. From the results shown in FIG. 5, the inventors concluded that ipsilateral hand movements are associated with earlier changes in the lower frequency spectra than with contralateral hand movements. FIG. 5A presents a bar histogram that shows the peak time of signal correlation with the active condition (time of cue presentation/movement against rest) averaged across the three subjects. Ipsilateral movements preceded similar changes with contralateral movements on average by 160 ms. FIG. 5B shows data from Subject 6 comparing the timing of the earliest significant electrode (activity vs. rest which had a p-value less than 0.001) for contralateral movement and for ipsilateral movement (electrode located over Brodman's area 9 BA9, which is part of the frontal cortex in the human brain). The dotted line indicates the average time of initiation of movement onset. Here one can see that ipsilateral cortical activity precedes movement while contralateral activity is after movement has begun. This activity is primarily in spectral changes below 30 Hz. This again demonstrates that significant power alteration occurs prior to contralateral hand movement and that this occurs in frequencies less than 30 Hz. These findings further demonstrate that both ipsilateral and contralateral motor processing occur on different time scales and support the notion that motor cortex is involved in a more motor planning role for ipsilateral hand movements.

As shown in FIGS. 5A and 5B, ipsilateral hand movements produce earlier changes than contralateral movements. In FIG. 5A, the peak of signal correlation with the movement of a hand-operated joystick was averaged for three subjects (1, 3, and 6). Ipsilateral hand movement preceded contralateral hand movement by 160 msec. In FIG. 5B, the data shows the progression of power alteration in frequencies between 0.5 HZ to 60 Hz for a significantly active electrode in Subject 6. The top figure is the significant power alteration associated with contralateral hand movement; the bottom figure shows the power change over time for ipsilateral hand movement. Time zero is the cue for which Subject 6 was instructed to initiate movement with the joystick. The dotted line is the initiation of movement. This data demonstrates that ipsilateral movements induce low frequency changes that precedes onset of movement and spectral changes associated with contralateral hand movements (which occur at the onset and during movement).

With data taken from Subjects 1, 3, and 6, those electrodes that demonstrated a statistically significant (p-values less than 0.001) power change when movement was compared to rest were included. The time period of 1000 ms after cue was presented was evaluated. The time of peak correlation of signal (at any frequency) with the active condition (measured with r2) was determined. FIG. 5B, in which bars represent standard deviation, illustrates data taken from an electrode over BA9 from Subject 6. Subject 6 performed a hand-controlled joystick task in which she would direct a cursor to a target on the periphery of the screen. This was performed using both the right hand and left hand. The time-series ECoG data was converted into the frequency domain using an autoregressive model. The spectrum was averaged for 1000 ms after cue for movement was presented. The correlation of power change for the respective frequency band was measured by the coefficient of determination, or r2 (r2 greater than 0.07 represents a p-value greater than 0.001, only significant spectral change shown). The dotted line represents the initiation of movement averaged from 80 trials.

Low-Frequency Spectra Encode Specific Motor Information

During experimentation, a hand-controlled force-feedback joystick task was utilized to further define the extent that the low frequencies associated with ipsilateral movements carry specific motor information. The task included a center-out task where the subject would direct and then hold (against force) the joystick-controlled cursor at fixed positions on targets at the periphery of the screen. The time-series ECoG data was converted into the frequency domain for the entire joystick task. The time that the cursor was held at upper and lower target positions was compared. Based on the results shown in FIG. 6, information specific to ipsilateral positional movements is more highly represented in low-frequency spectra than are contralateral movements. Additionally, the brain sites where processing occurs are distinct between ipsilateral and contralateral movements.

Figure 6:
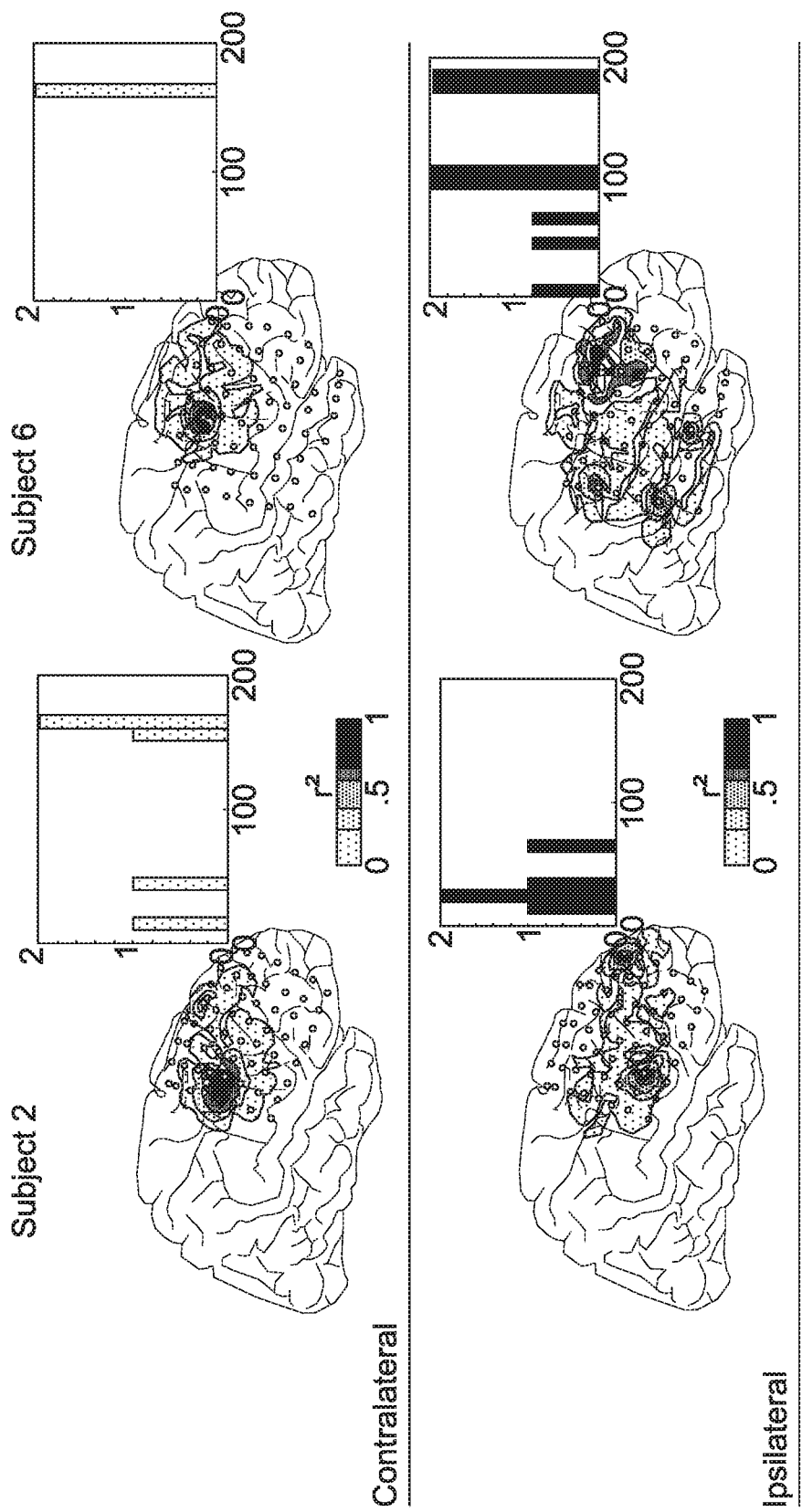
FIG. 6 shows graphs illustrating activations superimposed on stereotactic brains of two subjects and the spectra associated with those activation sites in accordance with the present invention.

FIG. 6 shows the data from two subjects (Subject 2 and Subject 6). The top row of FIG. 6 shows the sites (activations superimposed on a stereotactic brain) and the significant spectra (p greater than 0.001) associated with those activation sites (adjacent bar histograms). The top row shows the sites associated with up/down motor positioning when the contralateral hand is utilized. The activation sites are very similar in location between Subjects 2 and 6 in premotor cortex. The bottom row of FIG. 6 shows the sites associated with up/down motor positioning when the ipsilateral hand is utilized. Here the locations are inferior and anterior to the sites associated with contralateral hand control. The adjacent bar histograms show the number of electrodes found to be significantly correlated in differentiating position for the respective 10 Hz frequency bin. When the contralateral frequency distributions (top row) are compared to the ipsilateral frequency distributions (bottom row), there is an increased representation of lower frequencies that are either not present with contralateral movements (Subject 6) or at frequency bands distinct from those seen in contralateral processing (Subject 2). These findings demonstrate that the lower-frequency spectra convey significant information about specific ipsilateral motor actions. Additionally, they show that the sites associated with ipsilateral and contralateral motor processing are distinct.

As shown in FIG. 6, ipsilateral and contralateral motor processing occurs at anatomically distinct sites with increased lower frequency encoding for ipsilateral movements. The data shows the significant locations on the brain where brain activity has been localized when the up position of a hand-controlled joystick is compared against the down position. The adjacent bar graph plots the number of electrodes with frequency bands that have significant correlation in distinguishing between the up and down position (p-value greater than 0.001). For both Subjects 2 and 6 the location for contralateral processing is similar. The sites for ipsilateral processing are inferior. The frequencies associated with ipsilateral hand processing favor the lower frequencies, which are either not present with contralateral processing or at different bands. The figure represents data taken from Subjects 2 and 6. The subjects performed center-out joystick movements in which they would hold the cursor on the target for a fixed period of time. The time-series ECoG data from the period that they held the cursor at the top position and the bottom position was converted into the frequency domain using an autoregressive model and were compared against each other. The level of correlation of the signal oscillation for the up position (versus down) was measured by the coefficient of determination values, or r2. The data was summated across electrodes by placing a Gaussian kernel (diameter 5 mm) that was centered on the stereotactic coordinate of each electrode (derived from radiographs). The maximum of the kernel was determined by the respective r2 derived earlier and centered at the electrode locus. This allowed locations of correlation to be plotted into stereotactically derived spaced and summated. The adjacent bar graph is the number of electrodes plotted against 10 Hz frequency bins that showed significant correlation (p-value greater than 0.001).

Hemispheric Differences in Motor Processing

To define differences that may exist between hemispheres in contralateral and ipsilateral motor processing, data was summated from four Subjects (1, 2, 3, and 6) with homologously placed-grid arrays (two right-sided grids and two left-sided grids) onto a single stereotactic brain. Each of these subjects participated in right-hand and left-hand tasks. This consisted of the subject performing a minimum of six minutes of repetitive three-second hand tasks consisting of opening and closing the right hand or left hand on cue. Two specific frequency bands were analyzed: a low-frequency band (8-32 Hz) and a high-frequency band (75-100 Hz). Those electrode sites that showed spectral alteration in the high or low frequency band with a p-value greater than 0.001 were considered significant and plotted on the standardized brain. The results of this analysis are presented in FIG. 7B.

Figure 7A:
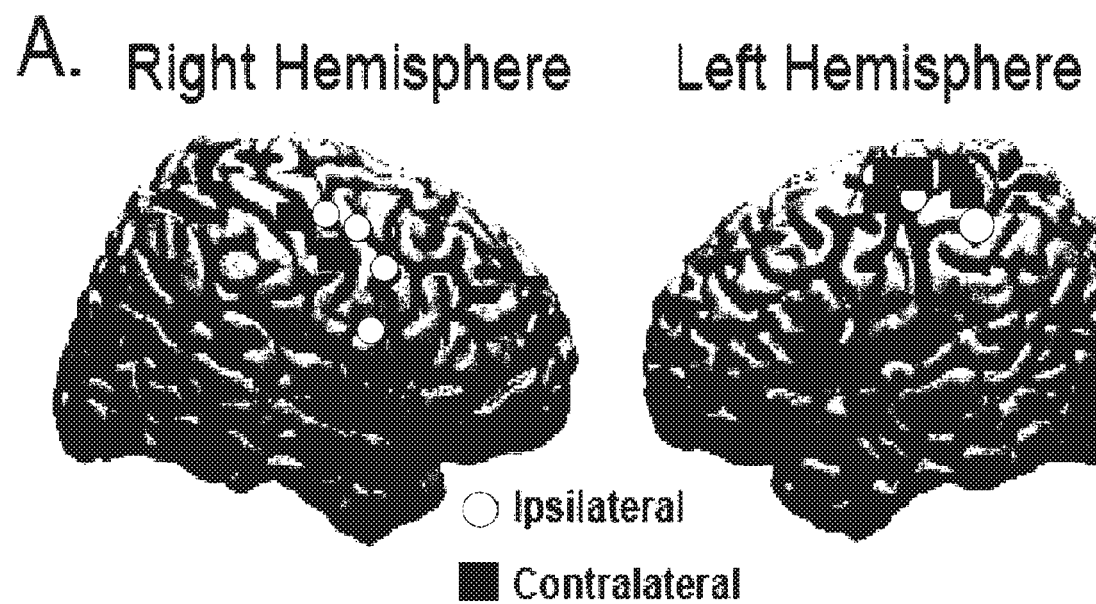
FIG. 7A shows hemispheric differences in motor processing between statistically significant electrode sites associated with ipsilateral and contralateral hand movements summated across four subjects in accordance with the present invention.

The electrodes that were significant (in either high or low frequency) and associated with ipsilateral hand movements are noted with circles and those associated with contralateral hand movements, with squares. The bar histogram shows the number of significant electrodes for the high-frequency and low-frequency band and whether they were significant with ipsilateral or contralateral hand movement. FIG. 7A illustrates that there is a different spatial distribution for motor movements on the right hemisphere and left hemisphere. The right hemisphere motor actions are more inferior to those of the left hemisphere. Additionally, ipsilateral movements have higher a proportion of significant electrodes associated with lower frequencies than contralateral movements (which are more highly represented in the higher frequencies). These findings show that the different hemispheres have a distinct localization for ipsilateral motor processing and further confirm the low-frequency representation of ipsilateral hand movements.

Figure 7B:
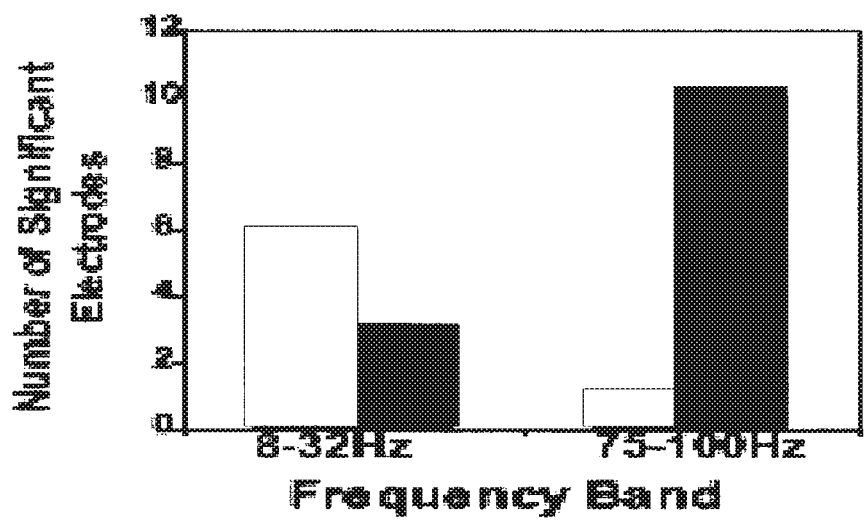
FIG. 7B is a bar histogram illustrating a number of electrodes for high-frequency and low-frequency bands and their significance with respect to ipsilateral or contralateral hand movements in accordance with the present invention.

FIGS. 7A and 7B show hemispheric differences in motor processing. In FIG. 7A, the data show the statistically significant electrode sites associated with ipsilateral (circles) and contralateral hand (squares) movements summated across four subjects (2 right/2 left) with subdural grid electrodes arrays. These anatomic differences are different for the given hemisphere in that right-side ipsilateral sites area more inferior than left-sided ipsilateral sites. This data supports that there are hemispheric differences in the cortical localization of ipsilateral hand movements. In FIG. 7B, the bar histogram shows the number of significant electrodes for the high-frequency and low-frequency bands and whether they were significant with ipsilateral or contralateral hand movement. The electrodes found to be significant with ipsilateral movement are more highly represented in the low-frequency band (8-32 Hz), while those found to be significant with contralateral movement were in the high-frequency band (75-100 Hz).

Data was taken from the four subjects who had hemispheric subdural grids placed (Subjects 1, 2, 3, and 6). Each subject performed a three-second hand task (opening and closing either right hand or left hand) interspersed by a rest period of equal time. All recorded ECoG data sets were referenced with respect to the common average. The time-series ECoG data was converted into the frequency domain using an autoregressive model. For this plot, low and high frequency bands were chosen (8-32 Hz and 75-100 Hz, respectively). Those electrodes with 0.75 or greater of the r2 maxima (p-value greater than 0.001) were considered significant. Radiographs were used to identify the stereotactic coordinates of each grid electrode (Fox, 1985), and cortical areas were defined using Talairach's Co-Planar Stereotaxic Atlas of the Human Brain (Talairach, 1988) and a Talairach transformation database. The significant electrodes were then plotted to a 3D cortical brain model from the AFNI SUMA web site.

Utilizing Brain Signals Unique to Ipsilateral Hand Movements for Device Control and Defining Dynamic Changes with Ongoing Performance The unique spectral and spatial electrophysiologic features associated with ipsilateral hand movements can be effectively utilized by a human subject to control an external device. This can be accomplished in isolation (ipsilateral hand movement alone), or in parallel with the physiologic operation of the contralateral limb. With ongoing control, these brain signals will demonstrate dynamic plasticity to improve performance.

Achieving Online Control of a Cursor with Ipsilateral and Contralateral Hand-Derived ECoG Signals.

To determine whether signals associated with ipsilateral hand movements could be utilized, three of the six subjects (1, 5, and 6) who performed hand screening tasks (as described above) also were tested in a real-time online task to use features associated with either ipsilateral or contralateral overt hand movements to control a cursor on a computer screen. The subjects received online feedback that consisted of one-dimensional vertical cursor movement controlled by ECoG features that had showed correlation with either the ipsilateral or contralateral hand movements during open-loop screening. The goal of the task was to hit one of two specified targets. Each subject achieved closed loop control twice, once using a contralateral hand task and a second time using an ipsilateral hand task. Based on the data presented in FIG. 9 and the table in FIG. 8, signals derived from ipsilateral motor movements can achieve high levels of control with final target accuracies between 70-96%.

This control is optimized when distinct locations and low-frequency spectra associated with ipsilateral movements are utilized, which was established in these three subjects by testing three different control scenarios:

1) Ipsilateral features used for control were different from contralateral features in both location and frequency spectra (Subject 1),
2) Ipsilateral features were in the same location using a high-frequency band (100 Hz) that overlapped for both ipsilateral and contralateral control (Subject 5), and
3) Ipsilateral features in same location but using different frequency spectra (ipsilateral—20 Hz, contralateral—100 Hz).

When low-frequency spectra was used for scenarios 1 and 3 (performance curves 1 and 3), high levels of control were achieved with ipsilateral hand movements (91% and 96% accuracies). In scenario 2 (performance curves 2), when overlapping high-frequency spectra (100 Hz) was used, the performance with ipsilateral hand movements was the worst with 70% target accuracy, while with contralateral movements a high level of control with 97% accuracy was still achieved. Scenario 2 (performance curves 2) also demonstrated the most disparate learning curves showing that high frequencies are less amenable to ipsilateral derived control than the lower frequencies. These preliminary findings by the inventors 1) were the first determination that ECoG signal derived from ipsilateral hand movements can be utilized for device control, and 2) they show that ipsilateral control signals can be differentiated from contralateral derived control features both in regards to cortical location and frequency spectra.

To understand how the change in performance was accounted for during online control, the change of correlation (as measured by r2) of the ECoG features, selected for control (specific frequency from specific electrode) over time, was examined. From the results shown in FIG. 9B, with ongoing control, the level of correlation of the control feature to the respective correct target increases. The progressive increase in correlation reflects the subject's ability to alter their cortical physiology with ongoing feedback. These changes occur over minutes and reflect a high level of cortical plasticity that can be induced by this methodology. The level of correlation was highest with contralateral tasks utilizing high frequencies (100 Hz). Correlations of control features with ipsilateral hand movements were highest when low frequency spectra (20-25 Hz) were utilized and lowest when high frequency spectra (100 Hz) were employed. These findings demonstrate the plastic nature of human cortical physiology in adapting to device control and emphasize the importance of lower-frequency spectra in their use for brain computer interface applications associated with ipsilateral hand processing.

Figure 9A:
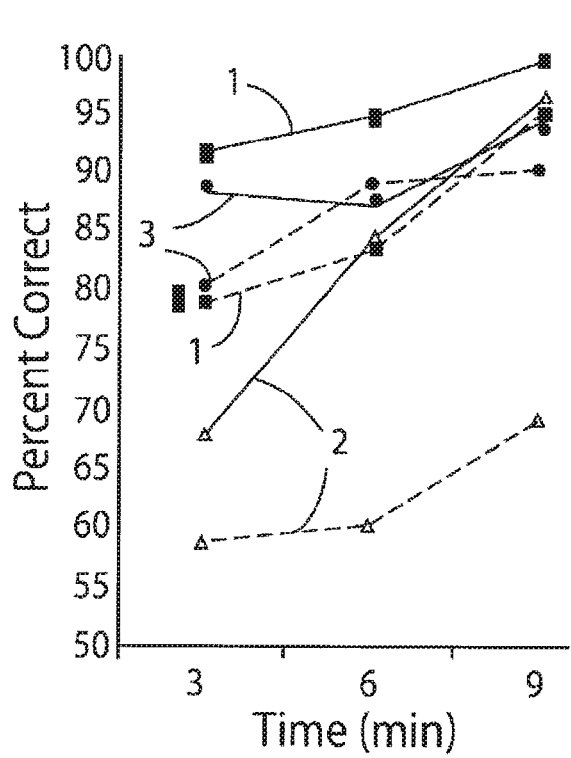
FIG. 9A is a graph illustrating performance curves that demonstrate the ability of three subjects to utilize signals from sensorimotor cortex associated with ipsilateral and contralateral hand movements to control a cursor on a computer screen in accordance with the present invention.
Figure 9B:
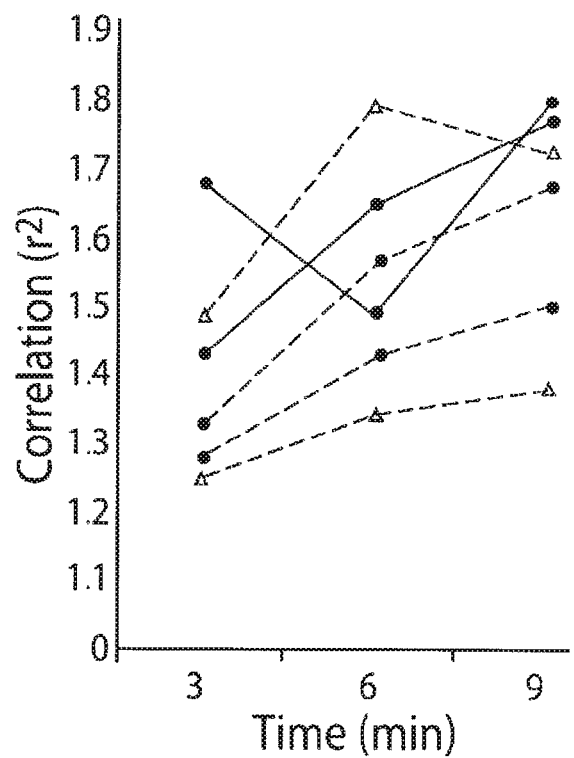
FIG. 9B is a graph illustrating tuning curves that demonstrate that for on-going controls the level of correlation between the control feature and the respective correct target in accordance with the present invention.

FIGS. 9A and 9B show utilizing signals associated with ipsilateral movements for external device control. FIG. 9A illustrates performance curves. The data indicates the ability of three subjects to utilize signals from sensorimotor cortex associated with either ipsilateral or contralateral hand movements to control a cursor on a computer screen. Each subject is distinct in what features were chosen to utilize for control:

Subject 1, different locations and different frequency spectra (ipsi—25 Hz, contra 100 Hz) were used;
Subject 5, identical locations and spectra were utilized (both utilized 100 Hz);
Subject 6, identical locations were used with different frequency spectra (ipsi—20 Hz, contra—100 Hz).

These results demonstrate that optimal control can be achieved using either distinct locations or distinct frequency spectra. Performance when high frequency is utilized with ipsilateral hand movements is not as robust.

FIG. 9B illustrates tuning curves. The data shows the level of correlation (as measured by r2) with the respectively chosen frequency band utilized for control with the respective targets. Over time all signals showed increased correlation demonstrating that these signals exhibit plastic changes with ongoing feedback. The subjects received online feedback that consisted of one-dimensional vertical cursor movement controlled by ECoG features that had showed correlation with either the ipsilateral or contralateral hand movements during open loop screening. For the ipsilateral limb and the contralateral limb there were three-minute runs. Each trial began with the appearance of a target that occupies either the top half or the bottom half of the right edge of the screen. One second later, the cursor appeared in the middle of the left edge of the screen and then moved steadily across the screen over a fixed period of 3.5 cm/sec with its vertical movement controlled continuously by the subject's ECoG features that were associated with either ipsilateral or contralateral hand movement. The subject's goal was to move the cursor vertically to the height of the target so that it hits the target when it reaches the right edge. The cursor movement was vertically controlled every 40 ms by a translation algorithm based on a weighted, linear summation of the amplitudes in the identified frequency bands from the identified electrodes for the previous 280 ms.

These preliminary studies 1) demonstrated that ipsilateral hand movements are associated with distinct anatomic and temporal profiles when compared to contralateral hand movements; 2) showed the cortical physiology associated with ipsilateral hand movements conveys very specific information about motor actions; 3) demonstrated that encoding of specific motor movements have a higher representation in lower frequencies than contralateral hand movements; 4) provided strong clues to different hemispheric localization in ipsilateral processing; 5) demonstrated for the first time that unique features associated with ipsilateral hand movements can be utilized by a human subject for effective device control; and 6) found that these control signals show a high level of plasticity in improving performance.

Figure 10:
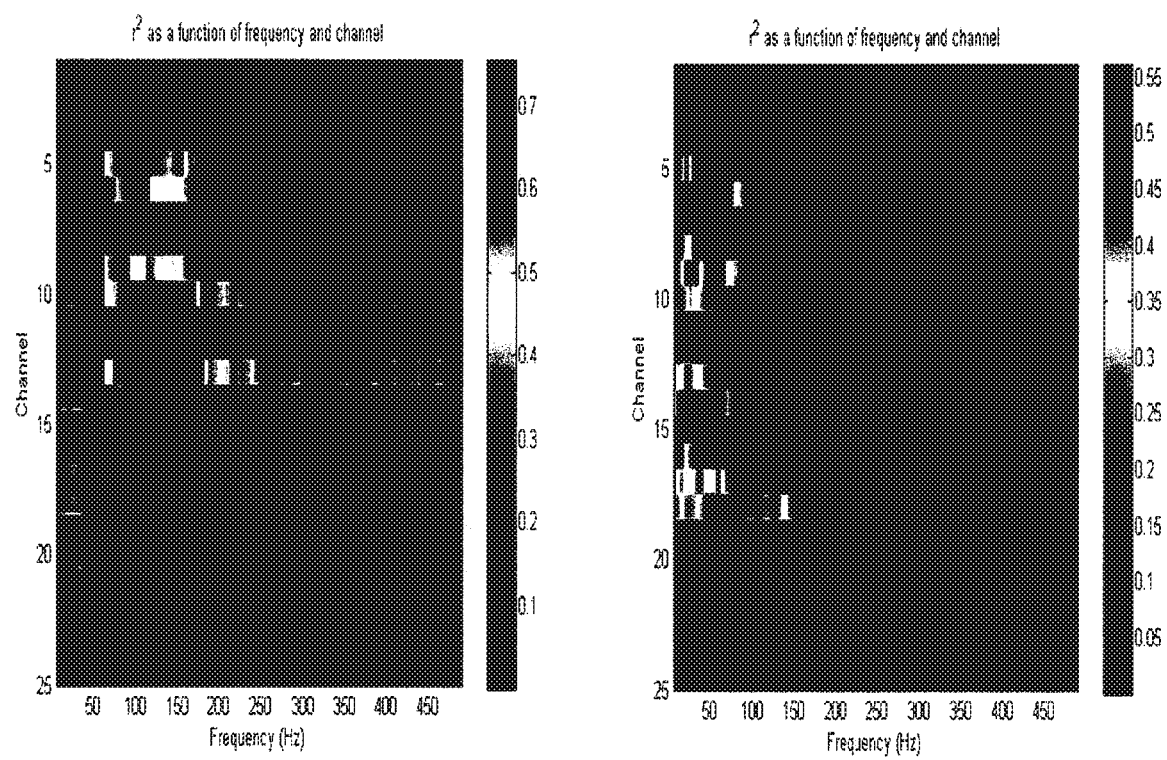
FIG. 10 shows two images that illustrate mapped activations when a subject performs contralateral and ipsilateral movements to move the left hand and the right hand, respectively, in accordance with the present invention.

FIG. 10 shows two images showing a feature plot where channel plotted against frequency. The color change is significant power changes that occurred when the active condition is compared against rest. The features plot on the left is the activation that is mapped when the subject who had a left hemispheric grid moved their right hand. The figure on the right is a features plot of when the subject with the same left hemispheric grid moved their left hand. As shown, the location and frequencies are very different between the two actions. Thus these different signals potentially can thus be utilized to control the contralateral arm naturally while using ipsilateral movements (real or imagined) to control something else in parallel.

Figure 11:
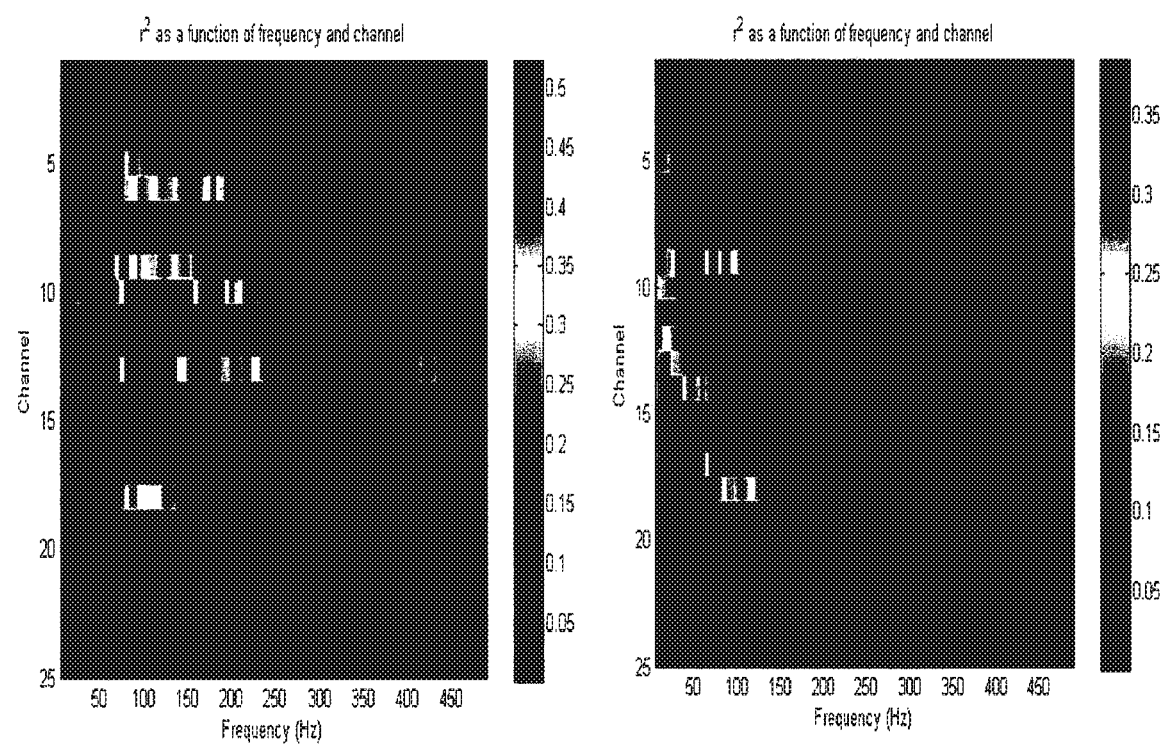
FIG. 11 shows two images that illustrate mapped activations when a subject performs contralateral and ipsilateral movements to control a cursor on a screen using brain signals alone in accordance with the present invention.

FIG. 11 shows two images showing a feature plot where channel plotted against frequency. The color change is significant power changes that occurred when the active condition is compared against rest. The features plot on the left is the activation that is mapped when the subject who had a left hemispheric grid moved their right hand to control a cursor on the screen using brain signals alone. The figure on the right is a features plot of when the subject with the same left hemispheric grid moved their left hand to control a cursor on the screen using brain signals alone. As shown, the location and frequencies are very different between the two actions. This result shows that the same hemisphere can be utilized to accomplish bisomatic control—a single hemisphere can control both the contra lateral side (as normal) and a device to facilitate and assist their non functioning side (ranging from simple computer devices, to robotic exoskeletons, to implanted electrodes in the body itself).

Methods, systems, and articles of manufacture consistent with the present invention could be commercially useful. For example, if an individual can control both sides of their body with a single hemisphere this would have enormous implications for people with hemispheric stroke. Since 72% stroke subjects have strokes involving a single side of their brain, developing a technology in which the healthy part of their brain can functionally compensate for the damaged portion could have significant impact.

Stroke is common. It is estimated 700,000 strokes occurred in the U.S. in 2002, 500,000 being first events and 200,000 recurrent strokes. If rates remain unchanged, it has been predict that 1,136,000 strokes will occur in the year 2025, associated mainly with the aging of the population. Though the majority of strokes occur in adult and elderly populations, it should be remembered that a significant number of strokes occur in children, particularly in the perinatal period. Stroke accounts for 1 in every 15 deaths in the U.S. In the U.S. in 2003, stroke accounted for approximately 158,000 deaths directly, a figure which rises to 273,000 if deaths in which stroke was a contributory cause are included. Stroke is also the leading cause of disability in the U.S. It has been estimated that in 2003 there were 5.5 million stroke survivors in the U.S. population. The financial burden of stroke is substantial. It has been estimated that for the U.S., the direct and indirect cost of stroke in 2006 will be $57.9 billion. Approximately 72% of stokes involve one side of the brain.

While various embodiments of the present invention have been described, it will be apparent to those of skill in the art that many more embodiments and implementations are possible that are within the scope of this invention. Accordingly, the present invention is not to be restricted except in light of the attached claims and their equivalents.

What is claimed is:

1. A system for assisting with movement of a body part affected by a stroke event, comprising:
 a brain signal acquisition system comprising a plurality of sensing devices that sense electrical brain signals from a brain of a subject having the body part affected by the stroke event, the plurality of sensing devices including sensing devices configured to sense electrical signals from a first hemisphere of the brain;
 a signal translating unit that translates the sensed electrical brain signals from the first hemisphere of the brain into a command signal for controlling the affected body part, wherein the affected body part is on a same side of a body as the first hemisphere of the brain, wherein the signal translating unit further identifies, from sensed electrical brain signals acquired from the first hemisphere of the brain during a closed-loop brain computer interface control mode of operation, a subset of the sensed electrical brain signals having at least one cortical feature associated with ipsilateral movement that is distinct from a cortical feature associated with contralateral movement; and
 a device that receives the command signal from the signal translating unit and assists with moving the body part in response to the command signal.

2. The system of claim 1, wherein the plurality of sensing devices sense electrical brain signals are selected from the group consisting of devices that sense electrocortigraphic (ECoG) signals, electroencephalography (EEG) signals, local field potentials, single neuron signals, (MEG) magnetoencephalography signals, mu rhythm signals, beta rhythm signals, low gamma rhythm signals, and high gamma rhythm signals.

3. The system of claim 2, wherein ECoG, EEG, local field potentials, and MEG signals include at least one of mu rhythm signals, beta rhythm signals, low gamma rhythm signals, and high gamma rhythm signals.

4. The system of claim 1, wherein the plurality of sensing devices sense electrical brain signals from one of a primary motor cortex, a premotor cortex, a frontal lobe, a parietal lobe, a temporal lobe, and an occipital lobe of the brain.

5. The system of claim 1, wherein the device that receives the command signal from the signal translating unit and assists with moving the body part is command signal is communicated to one of a robotic device, a transportation device, and a prosthetic control device.

6. The system of claim 1, wherein the device that receives the command signal from the signal translating unit and assists with moving the body part is an external robotic assist device.

7. The system of claim 1, wherein the device that receives the command signal from the signal translating unit and assists with moving the body part utilizes at least one of external nerve and muscle stimulators.

8. The system of claim 1, wherein the device that receives the command signal from the signal translating unit and assists with moving the body part utilizes at least one of internally implanted nerve and muscle stimulators.

9. The system of claim 1, wherein the body part comprises an arm of the subject on the same side of the subject as the first hemisphere of the brain, wherein the first hemisphere of the brain is largely unaffected by the stroke event, and wherein the device that assists in the movement of the body part assists in the movement of the arm.

10. The system of claim 9, wherein the device that assists in the movement of the arm is a robotic exoskeleton.

11. The system of claim 1, wherein the body part comprises a hand of the subject on the same side of the subject as the first hemisphere of the brain, wherein the first hemisphere of the brain is largely unaffected by the stroke event, and wherein the device that assists in the movement of the body part assists in the movement of the hand.

12. The system of claim 11, wherein the device that assists in the movement of the hand is a robotic exoskeleton.

13. The system of claim 1, wherein the signal translating unit converts the sensed electrical signals into a frequency domain and further determines spectral power changes for the sensed electrical signals in the frequency domain.

14. The system of claim 1, wherein the at least one cortical feature associated with ipsilateral movement is initially identified during an open-loop screening process during which the subject performs actual or imagined movements of both (i) ipsilateral movements comprising movements of the affected body part on the same side of the subject as the first hemisphere of the brain, and (ii) contralateral movements comprising movements of an unaffected body part on the opposite side of the subject from the first hemisphere of the brain.

15. The system of claim 1, wherein the at least one cortical feature associated with ipsilateral movement comprises spectral power changes being predominantly represented in a range of frequencies below 75 Hz.

16. The system of claim 15, wherein the cortical feature associated with contralateral movement comprises spectral power changes being predominantly represented in a range of frequencies at or above 75 Hz.

17. The system of claim 1, wherein the at least one cortical feature associated with ipsilateral movement comprises spectral power changes represented at an anterior/lateral location of the first hemisphere of the brain.

* * * * *